United States Patent [19]

Kamiya et al.

[11] 4,191,762

[45] Mar. 4, 1980

[54] 2-LOWER ALKYL-7-SUBSTITUTED AMINO-2 OR 3-CEPHEM-4-CARBOXYLIC ACID COMPOUNDS

[75] Inventors: Takashi Kamiya, Suita; Tsutomu Teraji; Masashi Hashimoto, both of Toyonaka; Osamu Nakaguti; Teruo Oku, both of Osaka, all of Japan

[73] Assignee: Fujisawa Pharmaceutical Co., Ltd., Osaka, Japan

[21] Appl. No.: 808,616

[22] Filed: Jun. 21, 1977

Related U.S. Application Data

[63] Continuation-in-part of Ser. No. 640,910, Dec. 15, 1975, Pat. No. 4,113,940, which is a continuation-in-part of Ser. No. 451,159, Mar. 14, 1974, abandoned.

[30] Foreign Application Priority Data

Jun. 28, 1976 [GB] United Kingdom ............... 26740/76
Jan. 5, 1977 [GB] United Kingdom .................. 262/77

[51] Int. Cl.$^2$ .......................................... C07D 501/20
[52] U.S. Cl. ........................................ 424/246; 544/22
[58] Field of Search ..................... 544/22, 77; 424/246

[56] References Cited

U.S. PATENT DOCUMENTS

| | | | |
|---|---|---|---|
| 3,578,660 | 5/1971 | Cooper | 544/16 |
| 3,708,480 | 1/1973 | Webber et al. | 544/16 |
| 3,799,938 | 3/1974 | Heusler et al. | 544/16 |
| 3,883,517 | 5/1975 | Heusler et al. | 544/16 |
| 4,008,246 | 2/1977 | Ochiai et al. | 544/27 |

FOREIGN PATENT DOCUMENTS 2412513  9/1974  Fed. Rep. of Germany.
2461933  7/1975  Fed. Rep. of Germany.
2556736  6/1976  Fed. Rep. of Germany.

OTHER PUBLICATIONS

McOmie, Protective Groups in Organic Chemistry, Chapter 2, Chapter 5 (1973), Plenum Press.

*Primary Examiner*—Nicholas S. Rizzo
*Attorney, Agent, or Firm*—Oblon, Fisher, Spivak, McClelland & Maier

[57] ABSTRACT

A compound of the formula:

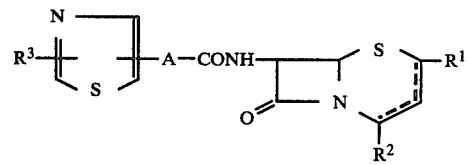

wherein
$R^1$ is ($C_1$ to $C_6$) alkyl,
$R^2$ is carboxy or a protected carboxy group,
$R^3$ is amino or a protected amino group, and
A is carbonyl or hydroxy ($C_1$ to $C_6$) alkylene, and pharmaceutically acceptable salt thereof, which is active against pathogenic bacteria, and methods for preparing the same.

13 Claims, No Drawings

2-LOWER ALKYL-7-SUBSTITUTED AMINO-2 OR 3-CEPHEM-4-CARBOXYLIC ACID COMPOUNDS

The present application is a continuation-in-part of Ser. No. 640,910, filed Dec. 15, 1975, now U.S. Pat. No. 4,113,940 which is in turn a continuation-in-part of Ser. No. 451,159, filed Mar. 14, 1974, now abandoned.

The present invention relates to new 2-lower alkyl-7-substituted amino-2 or 3-cephem-4-carboxylic acid compounds and pharmaceutically acceptable salts thereof. More particularly, it relates to new 2-lower alkyl-7-substituted amino-2 or 3-cephem-4-carboxylic acid compounds and pharmaceutically acceptable salts thereof which have antimicrobial activities and to process for the preparation thereof, to pharmaceutical composition comprising the same, and to a method of using the same therapeutically in the treatment of infectious diseases in human being and animals.

Accordingly, it is one object of the present invention to provide 2-lower alkyl-7-substituted amino-2 or 3-cephem-4-carboxylic acid compounds and pharmaceutically acceptable salts thereof, which are active against a number of pathogenic microorganisms.

Another object of the present invention is to provide processes for the preparation of 2-lower alkyl-7-substituted amino-2 or 3-cephem-4-carboxylic acid compounds and pharmaceutically acceptable salts thereof.

A further object of the present invention is to provide pharmaceutical composition comprising, as active ingredients, said 2-lower alkyl-7-substituted amino-2 or 3-cephem-4-carboxylic acid compounds and pharmaceutically acceptable salts thereof.

Still further object of the present invention is to provide a method for the treatment of infectious diseases caused by pathogenic bacteria in human being and animals.

The object 2-lower alkyl-7-substituted amino-2 or 3-cephem-4-carboxylic acid compounds are novel and can be represented by the following general formula (I).

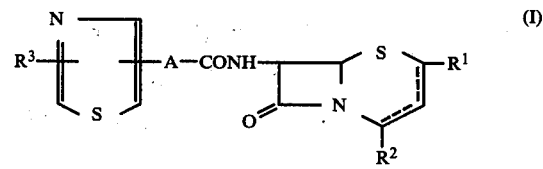

wherein
 $R^1$ is lower alkyl,
 $R^2$ is carboxy or a protected carboxy group,
 $R^3$ is amino or a protected amino group and
 A is carbonyl or hydroxy(lower)alkylene.

According to the present invention, the 2-lower alkyl-7-substituted amino-2 or 3-cephem-4-carboxylic acid compounds (I) can be prepared by various processes which are illustrated by the following schemes.

Process 1

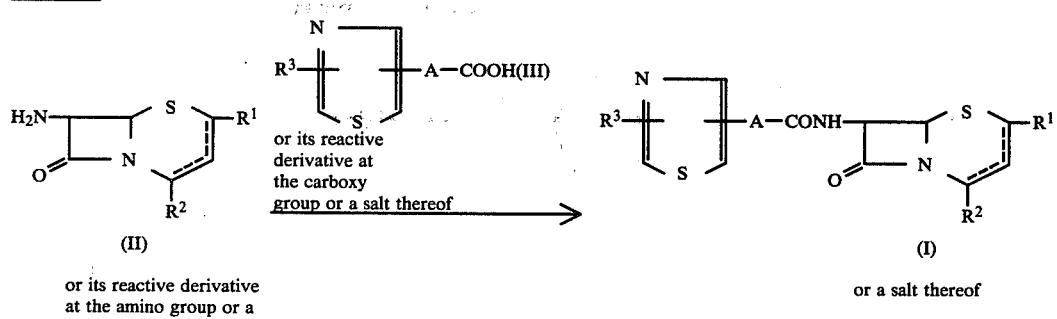

(II)
or its reactive derivative
at the amino group or a
salt thereof (I)
or a salt thereof Process 2

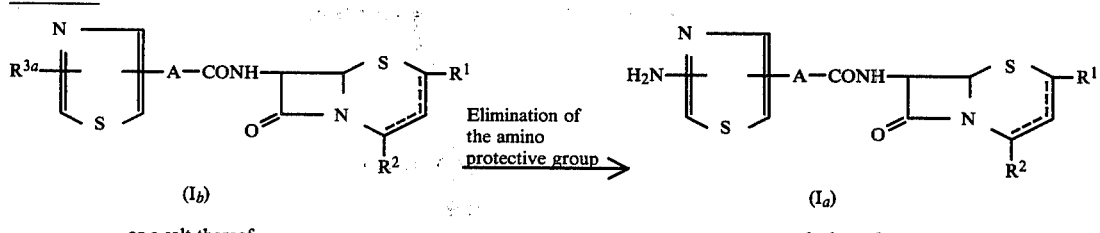

(I$_b$)
or a salt thereof (I$_a$)
or a salt thereof

Process 3

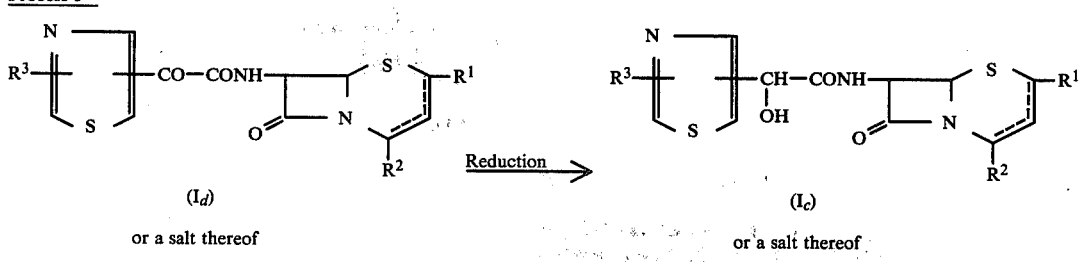

(I$_d$)
or a salt thereof (I$_c$)
or a salt thereof

Process 4

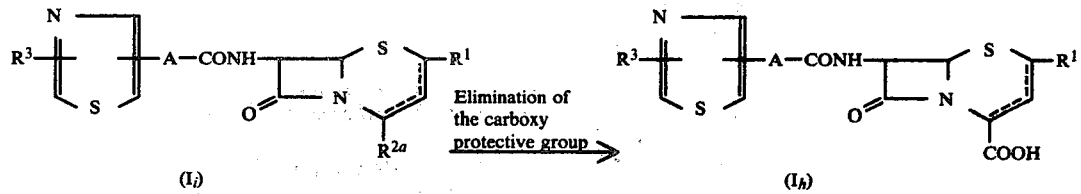

(I<sub>i</sub>)

or a salt thereof (I<sub>h</sub>)

or a salt thereof

Process 5

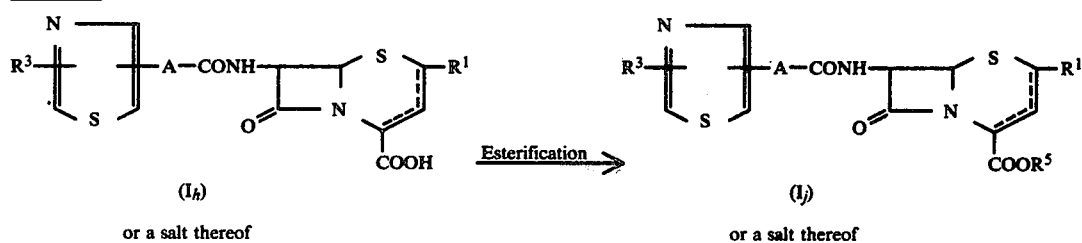

(I<sub>h</sub>)

or a salt thereof (I<sub>j</sub>)

or a salt thereof wherein
- $R^1$, $R^2$, $R^3$ and A are each as defined above,
- $R^{2a}$ is a protected carboxy group,
- $R^{3a}$ is a protected amino group and
- $R^5$ is an ester moiety of an esterified carboxy group represented by the formula: $-COOR^5$.

The starting compound (II) in the present invention can be prepared according to the methods described in W. German Offenlegungsschrift No. 2412513.

Among the starting compound (III) in the present invention, novel compounds can be prepared by the conventional processes which are illustrated by the following schemes.

is to be understood that they include tautomeric isomers. That is, in case that the group of the formula:

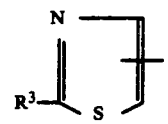

($R^3$ is as defined above) is contained in the molecules of said object and starting compounds, said group of the formula can be also alternatively represented by its tautomeric formula:

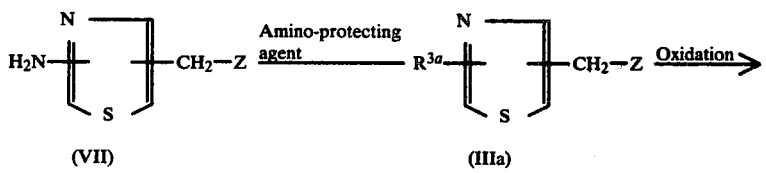

(VII)   (IIIa)

or its reactive derivative
at the amino group or a
salt thereof

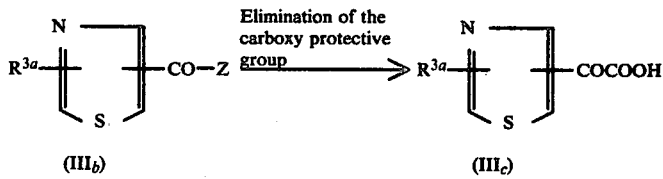

(III<sub>b</sub>)   (III<sub>c</sub>)

↓ Reduction

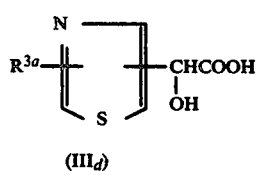

(III<sub>d</sub>)

wherein $R^{3a}$ is as defined above, and Z is a protected carboxy group.

Regarding the object compounds (I) and (Ia)–(Ij) and the starting compounds (III), (IIIa)–(IIId) and (VII), it

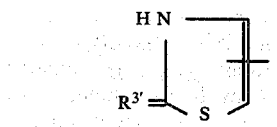

(R<sup>3'</sup> is imino or a protected imino group). That is, the both of said groups are in the state of equilibrium each other and such tautomerism can be represented by the following equilibrium.

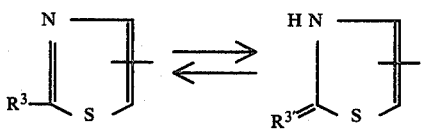

wherein $R^3$ and $R^{3'}$ are each as defined above.

These types of tautomerism between the amino-compound and the corresponding imino-compound as stated above have been well known in the literature, and it is obvious to be skilled in the arts that both of the tautomeric isomers are easily convertible reciprocally and are included within the same category of the compound per se. Accordingly, the both of the tautomeric forms of the object compounds (I) and $(I_a)$–$(I_j)$ and the starting compound (III), $(III_a)$–$(III_d)$ and (VII) are clearly included within the scope of the present invention. In the present specification and claims, the object and starting compounds including the group of such tautomeric isomers are represented by using one of the expressions therefor, that is the formula:

" 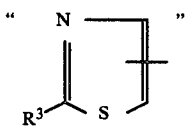 "

only for the convenient sake.

Suitable pharmaceutically acceptable salts of the object compounds (I) are conventional non-toxic salts and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable lower alkyl may include methyl, ethyl, propyl, isopropyl, butyl, pentyl, hexyl and the like.

Suitable protected carboxy may include an esterified carboxy and the like, and suitable examples of the ester moiety in said esterified carboxy may be the ones such as lower alkyl ester (e.g., methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, etc.), lower alkanesulfonyl(lower)alkyl ester (e.g., 2-mesylethyl ester, etc.) or mono(or di or tri)-halo(lower)alkyl ester (e.g., 2-iodoethyl ester, 2,2,2-trichloroethyl ester, etc.);

lower alkenyl ester (e.g., vinyl ester, allyl ester, etc.);

lower alkynyl ester (e.g., ethynyl ester, propynyl ester, etc.);

ar(lower)alkyl ester which may have at least one suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);

aryl ester which may have at least one suitable substituent(s) (e.g., phenyl ester, 4-chlorophenyl ester, tolyl ester, tertiarybutylphenyl ester, xylyl ester, mesityl ester, cumenyl ester, etc.), and the like.

Suitable protected amino may include an amino group substituted by a conventional protecting group such as acyl as mentioned below, ar(lower)alkyl which may have at least one suitable substituent(s) (e.g., benzyl, 4-methoxybenzyl, phenethyl, trityl, 3,4-dimethoxybenzyl, etc.) or the like.

Suitable acyl may include carbamoyl, aliphatic acyl group and acyl group containing an aromatic or heterocyclic ring. And, suitable examples of the said acyl may be lower alkanoyl (e.g., fomyl, acetyl, propionyl, butyryl, isobutyryl, valeryl, isovaleryl, oxalyl, succinyl, pivaloyl, etc.);

lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g., mesyl, ethanesulfonyl, propanesulfonyl, isopropanesulfonyl, butanesulfonyl, etc.);

arnesulfonyl (e.g., benzenesulfonyl, tosyl, etc.);

aroyl (e.g., benzoyl, toluoyl, naphthoyl, phthaloyl, indancarbonyl, etc.);

ar(lower)alkanoyl (e.g., phenylacetyl, phenylpropionyl, etc.);

ar(lower)alkoxycarbonyl (e.g., benzyloxycarbonyl, etc.), and the like.

The acyl moiety as stated above may have at least one suitable substituent(s) such as halogen (e.g., chlorine, bromine, iodine or fluorine), cyano, lower alkyl (e.g., methyl, ethyl, propyl, isopropyl, butyl, etc.), lower alkenyl (e.g., vinyl, allyl, etc.), or the like, suitable examples of which may be mono(or di or tri)halo(lower)alkanoyl (e.g., trifluoroacetyl, etc.).

Suitable lower alkylene moiety in the term "hydroxy(lower)alkylene" may include methylene, ethylene, trimethylene, propylene, tetramethylene and the like.

Suitable ester moiety of an esterified carboxy may include the ester exemplified for protected carboxy.

The various processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as acetoacetic acid or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can be optionally selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may be also used in a mixture with water.

When the compound (III) is used in free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N-carbonylbis-(2-methylimidazole), pentamethyleneketene-N-cyclohexylimine, diphenylketene-N-cyclohexylimine, ethoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intra-molecular salt, (chloromethylene)dimethylammonium chloride, 1-(p-chlorobenzenesulfonyloxy)-6-chloro-1H-benzotriazole, or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

Process 2

The object compound ($I_a$) or a salt thereof can be prepared by subjecting the compound ($I_b$) or a salt thereof to elimination reaction of the amino protective group.

Suitable salt of the compound ($I_b$) can be referred to the metal salt, ammonium salt and organic amine salt exemplified for the compound (II).

The elimination reaction is carried out in accordance with a conventional method such as hydrolysis, reduction, or the like. The hydrolysis may also include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid includes an organic or inorganic acid such as formic acid, trifluoroacetic acid, benzenesulfonic acid, p-toluenesulfonic acid, hydrochloric acid and the like, and the most suitable acid is an acid which can be easily removed from the reaction mixture by a conventional manner such as distillation under reduced pressure, for example, formic acid, trifluoroacetic acid, etc. The acids can be selected according to the kind of the protected group to be eliminated. When the elimination reaction is conducted with an acid, it can be carried out in the presence or absence of a solvent. Suitable solvent includes water, a conventional organic solvent or a mixture thereof. The hydrolysis using hydrazine is commonly applied for eliminating a phthaloyl type amino-protective group.

The reductive elimination is generally applied for eliminating the protective group, for example, haloalkoxycarbonyl (e.g., trichloroethoxycarbonyl, etc.), substituted or unsubstituted aralkoxy carbonyl (e.g., benzyloxycarbonyl, etc.), 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, prpionic acid, hydrochloric acid, etc.); and catalytic reduction. Suitable catalyst includes a conventional one, for example, Raney nickel, platinum oxide, palladium on charcoal and the like.

Among the protective groups, the acyl group can be generally eliminated by hydrolysis. Especially, trifluoroacetyl group can be easily eliminated by treating with water even in around neutral condition, and halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g., phosphorus oxychloride, etc.) and an iminoetherifying agent such as lower alkanol (e.g., methanol, ethanol, etc.), if necessary, followed by hydrolysis.

The reaction temperature is not critical and may be suitably selected in accordance with the kind of the protective group for the amino group and the elimination method as mentioned above, and the reaction is preferably carried out under a mild condition such as under cooling or at slightly elevated temperature.

The present invention includes, within its scope, the cases that the protected carboxy is transformed into the free carboxy group during the reaction or the post-treating step of the present process.

Process 3

The object compound ($I_c$) or a salt thereof can be prepared by reducing the compound ($I_d$) or a salt thereof.

Suitable salt of the compound ($I_d$) can be referred to the ones exemplified for the compound (II).

The present reduction is conducted by a conventional method such as a method of using an alkali metal borohydride (e.g., sodium borohydride, potassium borohydride, etc.) or the like.

The present reduction is usually carried out in a solvent which does not adversely influence the reaction, for example, water, methanol, ethanol, tetrahydrofuran, dioxane and the like. The present reduction can also be carried out in the presence of an inorganic or an organic base such as an alkali metal (e.g., sodium, potassium, etc.), an alkaline earth metal (e.g., magnesium, calcium, etc.), the hydroxide or carbonate or bicarbonate thereof, tri(lower)alkylamine (e.g., trimethylamine, triethylamine, etc.), picoline, N-methylpyrrolidine, N-methylmorpholine, 1,5-diazabicyclo[4,3,0]none-5-ene, 1,4-diazabicyclo[2,2,2]octane, 1,8-diazabicyclo[5,4,-0]undecene-7, or the like.

The reaction temperature is not critical and the present reaction is preferably carried out under a mild condition such as under cooling or slightly warming.

Process 4

The object compound ($I_h$) or a salt thereof can be prepared by subjecting the compound ($I_i$) or a salt thereof to elimination reaction of the carboxy protective group.

Suitable salt of the compound ($I_i$) can be referred to the acid addition salt exemplified for the compound (II).

In the present elimination reaction, all conventional methods used in the elimination reaction of the carboxy protective group, for example, hydrolysis, reduction, etc. are applicable. When the carboxy protective group is an ester, it can be eliminated by hydrolysis. The hydrolysis is preferably carried out in the presence of a base or an acid. Suitable base may include an inorganic base and an organic base as aforementioned in Process 2.

Suitable acid may include an organic acid (e.g., formic acid, acetic acid, propionic acid, etc.) and an inorganic acid (e.g., hydrochloric acid, hydrobromic acid, sulfuric acid, etc.). The reduction can be applicable to elimination of the protective group such as 2-iodoethyl ester, 2,2,2-trichloroethyl ester, or the like. The reduction applicable to the elimination reaction of the present invention may include, for example, reduction using a combination of a metal (e.g., zinc, zinc amalgam, etc.) or a chrome salt compound (e.g., chromous chloride, chromous acetate, etc.) and an organic or inorganic acid (e.g., acetic acid, propionic acid, hydrochloric acid, etc.), and reduction in the presence of a metallic catalyst. The metallic catalysts for the catalytic reduction include, for example, platinum catalyst (e.g., platinum wire, spongy platinum, platinum black, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), and the like.

The reaction temperature is not critical, and it may be suitably selected in accordance with the kind of the protective group of the carboxy and the elimination method.

Process 5

The object compound ($I_j$) or a salt thereof can be prepared by subjecting the compound ($I_h$) or a salt thereof to esterification reaction.

Suitable salt of the compound ($I_h$) can also be referred to the ones exemplified for the compound (II).

The esterifying agent to be used in the present reaction may be a compound of the formula: $X-R^5$ (XI) wherein $R^5$ is as defined above and X is hydroxy or reactive derivative thereof.

Suitable example of the reactive derivative of hydroxy may include a residue of an acid such as halogen (e.g., chlorine, bromine, iodine or fluorine) or the like.

The present reaction is usually carried out in a solvent such as dimethylformamide, pyridine, hexamethylphosphoric triamide, dioxane or other solvents which does not adversely affect the reaction.

In case that the compound ($I_h$) is used in a form of free acid, the reaction is preferably carried out in the presence of a base such as an inorganic base or an organic base as aforementioned in Process 2. The reaction temperature is not critical and the reaction is preferably carried out under cooling, at ambient temperature or under warming.

In the aforementioned reactions and/or the post-treating steps of the processes of the present invention, the aforementioned tautomeric isomers may occasionally transformed into the other tautomeric isomers, and such cases are also included in the scope of the present invention.

In case that the object compound (I) is obtained in a form of the free acid at 4 position and/or in case that the object compound (I) has a free amino group, it may be transformed into its pharmaceutically acceptable salt as aforementioned by a conventional method.

Processes for the preparation of the starting compounds are explained in detail as follows.

The starting compound (III$_a$) can be prepared by reacting the compound (VII) or its reactive derivative at the amino group or a salt thereof with an amino-protecting agent.

Suitable reactive derivative at the amino group of the compound (VII) and the suitable salt of the compound (VII) may include the same ones as illustrated in the explanations of the reactive derivative at the amino group of the compound (II) and salt of the compound (II), respectively.

Suitable amino-protecting agent may include acylating agent and the like.

Suitable acylating agent may include an aliphatic, aromatic and heterocyclic isocyanate, and the corresponding isothiocyanate, and an aliphatic, aromatic and heterocyclic carboxylic acid, and the corresponding sulfonic acid, carbonic acid ester and carbamic acid, and the corresponding thio acid, and the reactive derivative of the above acids.

Suitable reactive derivative of the above acids may include the same ones as illustrated in the explanation of "reactive derivative at the carboxy group of the compound (III)". The example of the protective group to be introduced into the amino group in the compound (VII) with the above amino-protecting agent may be the same ones as illustrated in the explanation of the protective group in the terms "a protected amino group."

The present reaction is carried out in the similar manner as illustrated in the reaction of the compound (II) or its reactive derivative at the amino group or a salt thereof with the compound (III) or its reactive derivative at the carboxy group.

The starting compound (III$_b$) can be prepared by oxidizing the compound (III$_a$).

The present oxidation reaction is conducted by a conventional method which is applied to the transformation of so-called activated methylene group into carbonyl group. That is, the present oxidation is conducted by a method, for example, by using a conventional oxidizing agent such as selenium dioxide, trivalent manganese compound (e.g. manganous acetate and potassium permanganate, etc.) or the like. The present oxidation is usually carried out in a solvent which does not adversely influence the reaction, for example, water, dioxane, tetrahydrofuran, and the like.

The reaction temperature is not critical and the reaction is preferably carried out under warming to heating.

The starting compound (III$_c$) can be prepared by subjecting the compound (III$_b$) to elimination reaction of the carboxy protective group.

The elimination reaction is carried out in the similar manner to that illustrated for the elimination reaction of Process 4.

The starting compound (III$_d$) can be prepared by reducing the compound (III$_c$).

The present reduction is carried out in the similar manner to that illustrated for the reduction of Process 3.

The object compounds (I) and pharmaceutically acceptable salt thereof of the present invention exhibit high antibacterial activity and inhibit the growth of a number of microorganisms including Gram-positive and Gram-negative bacteria.

For therapeutic purpose, the compounds according to the present invention can be used in the form of pharmaceutical preparation which contain said compounds, as an active ingredient, in admixture with a pharmaceutically acceptable carriers such as an organic or inorganic solid or liquid excipient suitable for oral, parenteral or external administration. The pharmaceutical preparations may be capsules, tablets, dragees, ointments or suppositories, solutions, suspensions, emulsions, and the like. If desired, there may be included in the above preparations auxiliary substances, stabilizing agents wetting or emulsifying agents, buffers and other commonly used additives.

While the dosage of the compounds will vary depend upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria.

In order to illustrate the usefulness of the object compounds, anti-microbial activities of some representative compounds of the present invention against some test strains of pathogenic bacteria are shown in their minimal inhibitory concentrations below.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of $\mu g/ml$. after incubation at 37° C. for 20 hours.

Test compounds (1) 2-Methyl-7-[2-(2-aminothiazol-4-yl)glyoxylamido]-3-cephem-4-carboxylic acid (Test compound (1))

(2) 2-Methyl-7-[2-hydroxy-2-(2-aminothiazol-4-yl)acetamido]-3-cephem-4-carboxylic acid (Test compound (2))

| Organism | Test Results | Test compound(1) | Test compound(2) |
|---|---|---|---|
| E.coli | No. 324 | 0.78 | 0.78 |
|  | No. 341 | 0.2 | 0.39 |
| Kl.aerogenes | No. 417 | 0.39 | 0.39 |
|  | No. 418 | 0.39 | 0.78 |
|  | No. 427 | 0.1 | 0.39 |
|  | No. 428 | 0.78 | 1.56 |
| Pr.minabilis | No. 501 | 0.78 | 1.56 |
|  | No. 520 | 0.39 | 1.56 |
|  | No. 525 | 6.25 | 1.56 |

The present invention is illustrated by the following examples.

PREPARATION OF THE STARTING COMPOUNDS

Preparation 1

(a) To acetic anhydride (384 ml.) was added dropwise formic acid (169.2 ml.) over 15 to 20 minutes under cooling below 35° C., and the mixture was stirred for 1 hour at 55° to 60° C. To the mixture was added ethyl 2-(2-aminothiazol-4-yl)acetate, which can be represented as ethyl 2-(2-imino-2,3-dihydrothiazol-4-yl)acetate, (506 g.) over 15 to 20 minutes under ice-cooling and stirring, and then the mixture was stirred for 1 hour at room temperature. After the reaction, the solvents were distilled off. To the residue was added diisopropyl ether (2500 ml.), and the mixture was stirred for 1 hour at room temperature. The precipitates were collected by filtration, washed with diisopropyl ether and then dried to give ethyl 2-(2-formylaminothiazol-4-yl)acetate, which can be represented as ethyl 2-(2-formylimino-2,3-dihydrothiazol-4-yl)acetate, (451.6 g.), mp 125° to 126° C. The remaining filtrate was concentrated, and the residue was washed with diisopropyl ether (500 ml.) and then dried to give further the same object compound (78.5 g.).

I.R. Spectrum (Nujol) 1737, 1700 cm$^{-1}$
N.M.R. Spectrum (CDCl$_3$, δ)
1.25 (3H, t, J=8 Hz)
3.7 (2H, s)
4.18 (2H, q, J=8 Hz)
6.9 (1H, s)
8.7 (1H, s)

(b) A mixture of manganous acetate tetrahydrate (120 g.), acetic acid (1000 ml) and acetic anhydride (100 ml.) was stirred for 20 minutes in an oil bath heated at 130° to 135° C., and to the mixture was added potassium permanganate (20 g.) over 5 minutes at 105° to 110° C. with stirring and then the mixture was further stirred for 30 minutes at 130° to 135° C. The mixture was cooled to room temperature, and to the mixture was added ethyl 2-(2-formylaminothiazol-4-yl)acetate, which can be represented as ethyl 2-(2-formylimino-2,3-dihydrothiazol-4-yl)acetate, (53.5 g.), and then the mixture was stirred for 15 hours at 38° to 40° C. under introduction of air at the rate of 6000 ml. per minute. After the reaction, the precipitates were collected by filtration. The precipitates were washed with acetic acid and water in turn and then dried to give ethyl 2-(2-formylaminothiazol-4-yl)glyoxylate, which can be represented as ethyl 2-(2-formylimino-2,3-dihydrothiazol-4-yl)glyoxylate, (41.5 g.), mp 232° to 233° C. (dec.).

(c) To a suspension of ethyl 2-(2-formylaminothiazol-4-yl)glyoxylate, which can be represented as ethyl 2-(2-formylimino-2,3-dihydrothiazol-4-yl)glyoxylate, (281 g.) in water (1100 ml.) was added an 1 N sodium hydroxide aqueous solution (2.23 l.) under stirring and ice-cooling, and then the mixture was stirred for 5 minutes at 10° to 15° C. After the reaction mixture was filtered, the filtrate was adjusted to pH 1 with concentrated hydrochloric acid with stirring. The precipitates were collected by filtration, washed with water and then dried to give 2-(2-formylaminothiazol-4-yl)glyoxylic acid, which can be represented as 2-(2-formylimino-2,3-dihydrothiazol-4-yl)glyoxylic acid, (234 g.), mp 133° to 136° C. (dec.).

N.M.R. Spectrum (NaDCO$_3$, δ)
8.27 (1H, s)
8.6 (1H, s)

Preparation 2

To a suspension of 2-(2-formylaminothiazol-4-yl)glyoxylic acid, which can be represented as 2-(2-formylimino-2,3-dihydrothiazol-4-yl)glyoxylic acid, (20 g.) in water (400 ml.) was added sodium bicarbonate (8.4 g.) under ice-cooling and stirring, and the mixture was stirred for 10 minutes at the same temperature, and then ethanol (10 ml.) was added thereto. To the mixture was added sodium borohydride (1.52 g.) over 10 minutes with stirring at the same temperature, and the mixture was stirred for 1 hour and 50 minutes at the same temperature. After the reaction, the reaction mixture was filtered. The filtrate was adjusted to pH 4.0 with 10% hydrochloric acid and then concentrated under reduced pressure till the volume became 100 ml. The concentrated filtrate was adjusted to pH 1 with 10% hydrochloric acid, and crystallization was induced by scratching. The concentrated filtrate was stirred for 1 hour at room temperature and then allowed to stand overnight in a refrigerator. The precipitates were collected by filtration, washed with ice-water twice and then dried under suction to give 2-hydroxy-2-(2-formylaminothiazol-4-yl)acetic acid, which can be represented as 2-hydroxy-2-(2-formylimino-2,3-dihydrothiazol-4-yl)acetic acid, (14.8 g.), mp. 188° to 189° C. (dec.).

I.R. Spectrum (Nujol) 1730, 1635 cm$^{-1}$
N.M.R. Spectrum (NaDCO$_3$, δ)
5.07 (1H, s)
7.15 (1H, s)
8.5 (1H, s)

EXAMPLE 1

To dimethylformamide (78 ml.) was added dropwise phosphorus oxychloride (11.9 g.) under stirring and ice-cooling, and the mixture was stirred for 30 minutes at 40° C. To the mixture was added 2-(2-formylaminothiazol-4-yl)glyoxylic acid, which can be represented as 2-(2-formylimino-2,3-dihydrothiazol-4-yl)glyoxylic acid, (7.8 g.) under cooling at −20° C., and then the mixture was stirred for 30 minutes under cooling at −20° to −15° C. Thus obtained mixture was added to a solution, which was prepared by stirring a mixture of 2-methyl-7-amino-3-cephem-4-carboxylic acid (8.35 g.) and bis(trimethylsilyl)acetamide (19.5 ml.) in dried methylene chloride (170 ml.) at room temperature, under cooling at −50° to −45° C. with stirring. The mixture was stirred for 1 hour at −45° to −40° C. and then the reaction mixture was poured into a solution of sodium bicarbonate (32 g.) in water (1.5 l) with shaking. The aqueous layer was separated and washed with ethyl acetate. The aqueous solution was layered with ethyl acetate and then adjusted to pH 1 to 2 with concentrated hydrochloric acid. The ethyl acetate layer was separated from the mixture, and the remaining aqueous layer was extracted with ethyl acetate (200 ml.×2). The ethyl acetate layers were combined together, washed with water and then concentrated to a small volume. The precipitates were collected by filtration, washed with a small amount of ethyl acetate and then dried to give 2-methyl-7-[2-(2-formylaminothiazol-4-yl)glyoxylamido]-3-cephem-4-carboxylic acid, which can be represented as 2-methyl-7-[2-(2-formylimino-2,3-dihydrothiazol-4-yl)glyoxylamido]-3-cephem-4-carboxylic acid, (7.9 g.), mp 210° to 215° C. (dec.).

I.R. Spectrum (Nujol) 3300, 3150, 1780, 1713, 1660, 1625, 1533 cm$^{-1}$
N.M.R. Spectrum (d$_6$-dimethylsulfoxide, δ)

| 1.45 | (3H, d, J = 7Hz, 2-CH$_3$) |
|---|---|
| 3.7–4.1 | (1H, m, 2-H) |
| 5.17 | (1H, d, J = 5Hz, 6-H) |
| 5.91 | (1H, dd, J = 5 and 8Hz, 7-H) |
| 6.59 | (1H, d, J = 6Hz, 3-H) |
| 8.40 | (1H, s, 5-H on thiazole ring) |
| 8.57 | (1H, s, OHC—N=) |
| 9.83 | (1H, d, J = 8Hz, 7-CONH) |

EXAMPLE 2

To a solution of thionyl chloride (3.01 g.) in methylene chloride (45 ml.) were added dimethylformamide (0.928 g.) and 2-(2-formylaminothiazol-4-yl)glyoxylic acid, which can be represented as 2-(2-formylimino-2,3-dihydrothiazol-4-yl)glyoxylic acid, (3.71 g.) in turn, and the mixture was stirred for 4 hours at room temperature. Thus obtained mixture was added over 5 minutes to a solution, which was prepared by stirring a mixture of 2-methyl-7-amino-3-cephem-4-carboxylic acid (3.3 g.) and trimethylsilylacetamide (16.2 g.) in methylene chloride (60 ml.) at room temperature for 40 minutes, with stirring under cooling to −25° to −20° C. The mixture was stirred for 30 minutes at −25° to −20° C., for 30 minutes at −10° to 0° C., and then for 30 minutes at room temperature. To the reaction mixture was added water (30 ml.), and the mixture was stirred for 10 minutes. After a saturated aqueous sodium bicarbonate solution was added to the mixture in order to dissolve the precipitates, the aqueous layer was separated. To the aqueous layer was added ethyl acetate, and the mixture was adjusted to pH 2 with 2 N hydrochloric acid, and then the ethyl acetate layer was separated. The remaining aqueous layer was further extracted with ethyl acetate. The ethyl acetate layers were combined together, washed with a saturated aqueous sodium chloride solution, dried over magnesium sulfate and then concentrated. Thus obtained crystalline residue was pulverized in diethyl ether, collected by filtration and then dried to give yellow crystalline powder of 2-methyl-7-[2-(2-formylaminothiazol-4-yl)glyoxylamido]-3-cephem-4-carboxylic acid, which can be represented as 2-methyl-7-[2-(2-formylimino-2,3-dihydrothiazol-4-yl)glyoxylamido]-3-cephem-4-carboxylic acid, (3.81 g.).

I.R. Spectrum (Nujol) 3475, 3315, 3200, 1788, 1655, 1620, 1530, 1293, 1240, 1185 cm$^{-1}$ N.M.R. Spectrum (d$_6$-dimethylsulfoxide, δ)

| 1.48 | (3H, d, J = 7Hz) |
|---|---|
| 3.70–4.17 | (1H, m) |
| 5.21 | (1H, d, J = 5Hz) |
| 5.96 | (1H, d, J = 5Hz) |
| 6.63 | (1H, d, J = 6Hz) |
| 8.44 | (1H, s) |
| 8.62 | (1H, s) |

Similarly, the following compounds were obtained.

(1) 2-Methyl-7-[2-hydroxy-2-(2-aminothiazol-4-yl)acetamido]-3-cephem-4-carboxylic acid hydrochloride, which can be represented as 2-methyl-7-[2-hydroxy-2-(2-imino-2,3-dihydrothiazol-4-yl)acetamido]-3-cephem-4-carboxylic acid hydrochloride, mp >250° C.

(2) 2-Methyl-7-[2-(2-aminothiazol-4-yl)glyoxylamido]-3-cephem-4-carboxylic acid hydrochloride, which can be represented as 2-methyl-7-[2-(2-imino-2,3-dihydrothiazol-4-yl)glyoxylamido]-3-cephem-4-carboxylic acid hydrochloride, mp >270° C.

EXAMPLE 3

To a suspension of 2-methyl-7-[2-(2-formylaminothiazol-4-yl)glyoxylamido]-3-cephem-4-carboxylic acid, which can be represented as 2-methyl-7-[2-(2-formylimino-2,3-dihydrothiazol-4-yl)glyoxylamido]-3-cephem-4-carboxylic acid, (3.0 g.) in methanol (60 ml.) was added dropwise phosphorus oxychloride (2.55 L g.) under ice-cooling and stirring, and the mixture was stirred for 3.5 hours at the same temperature and then for 30 minutes at room temperature. After the reaction, the reaction mixture was poured into diethyl ether (400 ml.). The precipitates were collected by filtration, washed with diethyl ether and then dried to give 2-methyl-7-[2-(2-aminothiazol-4-yl)glyoxylamido]-3-cephem-4-carboxylic acid hydrochloride, which can be represented as 2-methyl-7-[2-(2-imino-2,3-dihydrothiazol-4-yl)glyoxylamido]-3-cephem-4-carboxylic acid hydrochloride (2.2 g.), mp >270° C.

I.R. Spectrum (Nujol) 1770, 1700 (shoulder), 1665, 1624, 1515 cm$^{-1}$

N.M.R. Spectrum (d$_6$-dimethylsulfoxide, δ)

| 1.44 | (3H, d, J = 7Hz, 2-CH$_3$) |
|---|---|
| 3.6–4.1 | (1H, m, 2-H) |
| 5.15 | (1H, d, J = 5Hz, 6-H) |
| 5.82 | (1H, dd, J = 5 and 8Hz, 7-H) |
| 6.58 | (1H, d, J = 6Hz, 3-H) |
| 8.17 | (1H, s, 5-H on thiazole ring) |
| 9.87 | (1H, d, J = 8Hz, 7-CONH) |

Similarly, the following compound was obtained.

(1) 2-Methyl-7-[2-hydroxy-2-(2-aminothiazol-4-yl)acetamido]-3-cephem-4-carboxylic acid hydrochloride, which can be represented as 2-methyl-7-[2-hydroxy-2-(2-imino-2,3-dihydrothiazol-4-yl)acetamido]-3-cephem-4-carboxylic acid hydrochloride, mp 250° C.

EXAMPLE 4

To a suspension of 2-methyl-7-[2-(2-aminothiazol-4-yl)glyoxylamido]-3-cephem-4-carboxylic acid hydrochloride, which can be represented as 2-methyl-7-[2-(2-imino-2,3-dihydrothiazol-4-yl)glyoxylamido]-3-cephem-4-carboxylic acid hydrochloride, (3.80 g.) in methanol (70 ml.) was added 1 N sodium hydroxide aqueous solution (18.8 ml.) under ice-cooling and stirring. To the mixture was added sodium borohydride (0.13 g.) over 20 minutes under ice-cooling and stirring and the mixture was stirred for 30 minutes at the same temperature. After the reaction, methanol was distilled off from the reaction mixture. To the residue was added cold water (60 ml.), and the mixture was washed with ethyl acetate, adjusted to pH 2 with 10% hydrochloric acid and then filtered. The filtrate was subjected to column chromatography (non-ionic adsorption resin, Diaion HP 20 prepared by Mitsubishi Chemical Industries) and the column was washed with water and then eluted with 10% aqueous isopropyl alcohol solution. The eluates containing the object compound were collected and then lyophilized to produce pale yellow powder. (1.80 g.). To the powder were added methanol (10 ml.) and 35% hydrochloric acid (0.5 g.) in turn, and thus obtained solution was subjected to column chromatography using activated carbon (2.0 g.) and then the column was eluted with methanol. The eluates containing the object compound were collected and then the solvent was distilled off under reduced pressure. The residue was washed with ethyl acetate and then dried to give 2-methyl-7-[2-hydroxy-2-(2-aminothiazol-4-yl)acetamido]-3-cephem-4-carboxylic acid hydrochloride, which can be represented as 2-methyl-7-[2-hydroxy-2-(2-imino-2,3-dihydrothiazol-4-yl)acetamido]-3-cephem-4-carboxylic acid hydrochloride, (1.10 g.), mp >250° C.

I.R. Spectrum (Nujol) 3000–3400, 1775, 1690, 1630, 1523 cm$^{-1}$

N.M.R. Spectrum (d$_6$-dimethylsulfoxide, δ)

| 1.48 | (3H, d, J = 8Hz, 2-CH$_3$) |
|---|---|

-continued

| | |
|---|---|
| 3.5–4.1 | (1H, m, 2-H) |
| 5.09 | (1H, d, J = 5Hz, 6-H) |
| 5.17 (s) and 5.19 (s) | (—CHCO—N=) (Total : 1H) <br>            \| <br>            O— |
| 5.78 | (1H, dd, J = 5 and 9Hz, 7-H) |
| 6.54 | (1H, d, J = 6Hz, 3-H) |
| 6.76 | (1H, s, 5-H on thiazole ring) |
| 8.73 (d, J = 9Hz) and 8.81 (d, J = 9Hz) | (7-CONH) (Total : 1H) |

What is claimed is:

1. A compound of the formula:

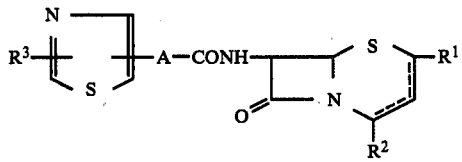

wherein
$R^1$ is ($C_1$ to $C_6$) alkyl,
$R^2$ is carboxy or a carboxy group protected by an eliminatable protective group, and
$R^3$ is amino or amino group protected by an eliminatable protective group and
A is carbonyl or hydroxy ($C_1$ to $C_6$) alkylene, and pharmaceutically acceptable salt thereof.

2. The compound of claim 1, wherein
$R^1$ is ($C_1$ to $C_6$) alkyl,
$R^2$ is carboxy or a carboxy group protected by an eliminatable protective esterifying group,
$R^3$ is amino or an amino group protected by an eliminatable protective acyl group and
A is carbonyl.

3. The compound of claim 2, wherein
$R^1$ is ($C_1$ to $C_6$) alkyl,
$R^2$ is carboxy, ($C_1$ to $C_6$) alkoxycarbonyl which may have 1 to 3 halogen atom(s) or ($C_1$ to $C_6$) alkanoyloxy-($C_1$ to $C_6$) alkoxycarbonyl,
$R^3$ is amino or ($C_1$ to $C_6$) alkanoylamino which may have 1 to 3 halogen atom(s) and
A is carbonyl.

4. The compound of claim 3, wherein
$R^2$ is carboxy and
$R^3$ is amino.

5. The compound of claim 4, which is 2-methyl-7-[2-(2-aminothiazol-4-yl)glyoxylamido]-3-cephem-4-carboxylic acid or its hydrochoride.

6. The compound of claim 3, wherein
$R^2$ is carboxy and
$R^3$ is ($C_1$ to $C_6$) alkanoylamino which may have 1 to 3 halogen atom(s).

7. The compound of claim 6, which is 2-methyl-7-[2-(2-formylaminothiazol-4-yl)glyoxylamido]-3-cephem-4-carboxylic acid.

8. The compound of claim 1, wherein
$R^1$ is ($C_1$ to $C_6$) alkyl,
$R^2$ is carboxy or a carboxy group protected by an eliminatable protective esterifying group,
$R^3$ is amino or an amino group protected by an eliminatable protective acyl group and
A is hydroxy ($C_1$ to $C_6$) alkylene.

9. The compound of claim 8, wherein
$R^1$ is ($C_1$ to $C_6$) alkyl,
$R^2$ is carboxy, ($C_1$ to $C_6$) alkoxycarbonyl which may have 1 to 3 halogen atom(s) or ($C_1$ to $C_6$) alkanoyloxy-($C_1$ to $C_6$) alkoxycarbonyl,
$R^3$ is amino or ($C_1$ to $C_6$) alkanoylamino which may have 1 to 3 halogen atom(s) and
A is hydroxy ($C_1$ to $C_6$) alkylene.

10. The compound of claim 9, wherein
$R^2$ is carboxy and
$R^3$ is amino.

11. The compound of claim 10, which is 2-methyl-7-[2-hydroxy-2-(2-aminothiazol-4-yl)acetamido]-3-cephem-4-carboxylic acid or its hydrochloride.

12. A pharmaceutical composition for the treatment of infectious disease caused by pathogenic bacteria comprising a compound of claim 1 or pharmaceutically acceptable salt thereof in association with a pharmaceutically acceptable, substantially non-toxic carrier or excipient.

13. A method for producing a pharmaceutical composition for the treatment of infectious disease caused by pathogenic bacteria which comprises mixing a compound of claim 1 or pharmaceutically acceptable salt thereof as an active ingredient with an inert carrier.

* * * * *